United States Patent
Idelevich et al.

(10) Patent No.: US 10,018,622 B2
(45) Date of Patent: *Jul. 10, 2018

(54) METHODS AND KITS FOR DIFFERENTIAL STAINING OF ABNORMAL URINARY SYSTEM CELLS

(71) Applicant: Zetiq Technologies LTD., Tel Aviv (IL)

(72) Inventors: Pavel Idelevich, Rehovot (IL); Adi Elkeles, Tel Mond (IL); Dov Terkieltaub, Ramat Gan (IL); Ami Eyal, Ramat Gan (IL); Dan Jacob Gelvan, Ramat Hasharon (IL)

(73) Assignee: ZETIQ TECHNOLOGIES LTD., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/715,559

(22) Filed: May 18, 2015

(65) Prior Publication Data

US 2015/0253310 A1   Sep. 10, 2015

Related U.S. Application Data (63) Continuation-in-part of application No. 13/900,055, filed on May 22, 2013, now abandoned, which is a continuation of application No. PCT/IL2011/050016, filed on Nov. 17, 2011, application No. 14/715,559, which is a continuation-in-part of application No. 13/673,643, filed on Nov. 9, 2012, now Pat. No. 9,057,092, which is a continuation-in-part of application No. 12/224,792, filed as application No. PCT/IL2007/000281 on Mar. 6, 2007, now Pat. No. 8,343,733.

(60) Provisional application No. 61/415,893, filed on Nov. 22, 2010, provisional application No. 60/778,839, filed on Mar. 6, 2006, provisional application No. 60/778,944, filed on Mar. 6, 2006, provisional application No. 60/778,900, filed on Mar. 6, 2006, provisional application No. 60/778,902, filed on Mar. 6, 2006.

(51) Int. Cl.
| | |
|---|---|
| *G01N 33/574* | (2006.01) |
| *G01N 33/50* | (2006.01) |
| *G01N 1/30* | (2006.01) |
| *G01N 33/569* | (2006.01) |

(52) U.S. Cl.
CPC .......... *G01N 33/5091* (2013.01); *G01N 1/30* (2013.01); *G01N 33/56966* (2013.01); *G01N 33/57407* (2013.01)

(58) Field of Classification Search
None
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris et al. |
| 3,996,345 A | 12/1976 | Ullman |
| 4,034,074 A | 7/1977 | Miles |
| 4,036,945 A | 7/1977 | Haber |
| 4,098,876 A | 7/1978 | Piasio et al. |
| 4,331,647 A | 5/1982 | Goldenberg |
| 4,666,828 A | 5/1987 | Gusella |
| 4,683,202 A | 7/1987 | Mullis |
| 4,698,360 A | 10/1987 | Masquelier |
| 4,801,531 A | 1/1989 | Frossard |
| 4,879,219 A | 11/1989 | Wands et al. |
| 4,946,778 A | 8/1990 | Ladner et al. |
| 5,011,771 A | 4/1991 | Bellet et al. |
| 5,192,659 A | 3/1993 | Simons |
| 5,272,057 A | 12/1993 | Smulson et al. |
| 5,281,521 A | 1/1994 | Trojanowski et al. |
| 6,051,393 A | 4/2000 | Jones et al. |
| 6,284,543 B1 | 9/2001 | Alvarez |
| 8,012,678 B2 | 9/2011 | Pyeon et al. |
| 2002/0058028 A1 | 5/2002 | Malmros et al. |
| 2004/0260157 A1 | 12/2004 | Montes |

(Continued)

FOREIGN PATENT DOCUMENTS

| | | |
|---|---|---|
| WO | 9616334 A2 | 5/1996 |
| WO | 03091729 A1 | 11/2003 |

(Continued)

OTHER PUBLICATIONS

Achilonu et al., (2008) Synthesis of Proanthocyanidins. Part 1. The First Oxidative Formation of the Interflavanyl Bond in Procyanidins. Organic Letters 10 (17): 3865- 3868.

Anantaraman and Ravindranath (1976) Histochemical characteristics of the egg envelopes of *Acanthosentis* sp. (Acanthocephala). Z Parasitenkd 48(3-4): 227-38

Desmedt et al., (2009) Quantitation of HER2 expression or HER2:HER2 dimers and differential survival in a cohort of metastatic breast cancer patients carefully selected for trastuzumab treatment primarily by FISH. Diag Mol Pathol 18(1):22-29.Translated abstract.

Dilek et al., (1998) Mucin production in carcinomas of the uterine cervix. Exp J Obstet Gynecol 79: 149-151.

(Continued)

*Primary Examiner* — Mark Halvorson
(74) *Attorney, Agent, or Firm* — The Roy Gross Law Firm, LLC; Roy Gross (57) ABSTRACT

Methods and kits for identifying abnormal urinary system cells in a sample, by contacting the cells or the sample containing same with a combination of an extract from a *Ficus* plant, or one or more components thereof, an acidic dye and a basic dye.

14 Claims, 6 Drawing Sheets
(6 of 6 Drawing Sheet(s) Filed in Color)

(56) References Cited

U.S. PATENT DOCUMENTS

| | | | |
|---|---|---|---|
| 2005/0181429 A1 | 8/2005 | Fejgin et al. | |
| 2009/0117610 A1 | 5/2009 | Gelvan et al. | |
| 2009/0221430 A1 | 9/2009 | Wu et al. | |
| 2011/0318756 A1* | 12/2011 | Tsivis | G01N 1/30 435/7.21 |

FOREIGN PATENT DOCUMENTS

| | | |
|---|---|---|
| WO | 2004086937 A2 | 10/2004 |
| WO | 2007015926 A2 | 2/2007 |
| WO | 2007102146 A2 | 9/2007 |
| WO | 2009055052 A2 | 4/2009 |

OTHER PUBLICATIONS

Duesbery et al., (2001) Suppression of ras-mediated transformation and inhibition of tumor growth and angiogenesis by anthrax lethal factor, a proteolytic inhibitor of multiple MEK pathways. Proc Natl Acad Sci U S A 98(7): 4089-94.

Fukuda et al., (1980) Fluorescence fading and stabilization in cytofluorometry. Histochem 65: 269-276.

Hamburger and Hamilton (1951) A series of normal stages in the development of the chick embryo. J Morphol 88(1): 49-92.

Idelevich et al., (2009) Novel Histochemical Stain for Tinctorial Detection of Cancer and Neoplastic Cells. The Journal of Histotechnology 32(3):97-105.

Klein et al., (2005) Transitional cell hyperplasia and carcinomas in urinary bladders of transgenic mice with keratin 5 promoter-driven cyclooxygenase-2 overexpression. Cancer Res 65(5): 1808-1813.

Komen et al., (2008) Viability analysis and apoptosis induction of breast cancer cells in a microfluidic device: effect of cytostatic drugs. Biomed Microdevices 10(5):727-737.

Kortekangas-Savolainen et al., (2006) Allergens of Ficus Benjamina (weeping fig):Unique allergens in sap. Allergy 61(3)393-394.

Molnar and Mehes (2009) Predictive molecular pathological testing in the diagnosis of high-grade tumors of glial origin. Magyer Oncologia 53(1):33-38.Translated abstract.

Nifli et al., (2005) Monomeric and oligomeric flavanols are agonists of membrane androgen receptors. Exp Cell Res 309(2): 329-339.

Pan et al., (2001) Comparative study on liquid-based cytology for cervical carcinoma screening in a higlr risk area of China. Chinese Journal of Oncology 23(4): 309-312. Abstract.

Papanicolaou and Traut (1941) The diagnostic value of vaginal smears in carcinoma of the uterus. Am J Obstet Gynecol 42: 193-206.

Proctor et al., (2010) Biomarkers in bladder cancer. Histopathology 57(1): 1-13.

Scholzen and Gerdes (2000) The Ki-67 protein: from the known and the unknown. J Cell Physiol 182(3): 311-322.

Shao et al., (2003) Grape seed proanthocyanidin extract attenuates oxidant injury in cardiomyocytes. Pharmacological Research 47: 463-469.

Steven et al., (1996) Fluorescent location of cells of cytological interest in cervical smears prestained with thionin. Anticancer Res 16(3A):1193-1196.

Trunk et al., (2004) Morphologic characteristics of p16lNK4a-positive cells in cervical cytology samples. Acta Cytol 48(6): 771-82.

Ye et al., (1999) The cytotoxic effects of a novel IH636 grape seed proanthocyanidin extract on cultured human cancer cells. Mol Cell Biochem 196(1-2):99-108.

Zhang et al., (2005) Proanthocyanidin from grape seeds potentiates anti-tumor activity of doxorubicin via immunomodulatory mechanism. Int Immunopharmacol 5(7-8): 1247-1257.

Database Biosis [online] Bioscience Information Service, Philadelphia, PA, US; 1986, Sackeyfio, A. C. et al: "The anti-inflammatory effect of a crude aqueous extract of the root bark of Ficus-Elastica in the rat" Dtabase accession No. PREV198682095850 abstract & Archives Internationales de Pharmacodynamie et de Therapie 281(1): 169-176.

"Staining" Wikipedia, the free incyclopedia retrieved from http://en.wikipedia.org/wiki/staining Nov. 8, 2010 (9 pages).

* cited by examiner

METHODS AND KITS FOR DIFFERENTIAL STAINING OF ABNORMAL URINARY SYSTEM CELLS

FIELD OF THE INVENTION

The present invention relates to methods and kits for identifying abnormal urinary system cells in a sample, by contacting the cells or the sample containing same with a combination of an extract from a *Ficus* plant, or one or more components thereof, an acidic dye and a basic dye.

BACKGROUND OF THE INVENTION

The urinary system (also called the excretory system or urinary tract) is the system that produces, stores, and eliminates urine. In humans it includes two kidneys, two ureters, the bladder, and the urethra. The urinary bladder is a hollow muscular and distensible organ that collects urine excreted by the kidneys before disposal by urination. Urinary bladder tissue and in particular the epithelial lining of the lower urinary tract (ureters, urinary bladder, and urethra), which is collectively referred to as the urothelium, is susceptible to numerous types of pathologies characterized by abnormal/atypical cells including lesions, tumors and cancers.

Since abnormal urothelial cells can be an indication of urothelial cancer, early identification of such cells and monitoring of diagnosed individuals can be used to prevent or effectively treat life threatening pathologies.

Bladder cancer refers to any of several types of malignant growths of the urinary bladder. It is a disease in which abnormal cells multiply without control in the bladder. The most common type of bladder cancer, transitional cell carcinoma (TCC), begins in the urothelium.

Carcinoma of the urinary bladder occurs with an incidence of 15 cases per 100,000 persons in the general population. It is the fourth most common cancer in males and its frequency is 3 times higher in males than in females. Over 90% of newly diagnosed bladder cancers are transitional cell carcinomas. The 5-year survival rate is ~95% when the tumor is confined to the bladder, and decreases to 46% and 6% when spreading locally or to distant sites, respectively, emphasizing the need for an effective early detection tool.

The current "gold standard" for detection of bladder cancer includes urine cytology and cystoscopy. Cystoscopic examination is an invasive test and is associated with relatively high costs, and urine cytology has low sensitivity, particularly in low-grade superficial TCC. Many clinical studies are underway with the aim of introducing new molecular markers in urine samples for the detection of TCC. These tests are potentially costly and thus pose a challenge for applicability as a general screening tool.

Thus, there is a need for an accurate method of detecting bladder cancer, especially in the early stages thereof.

SUMMARY OF THE INVENTION

Objects of the invention are directed to methods and kits for identifying abnormal urinary system cells in a sample of urinary system cells and use thereof in diagnosing a pathology such as bladder cancer. In some embodiments, a method of identifying abnormal urinary system cells in a urine sample is provided, the method comprising the steps of:
 (a) contacting the urine sample with a *Ficus* plant extract or one or more components;
 (b) staining the urine sample with a basic dye and acidic dye; and
 (c) identifying urinary system cells having a cytoplasm stained with a predominantly pink to red color as abnormal urinary system cells.

In some embodiments, the *Ficus* plant extract may be an ethanol extract of leaf tissue.

In some embodiments, the *Ficus* plant may be of a subgenus selected from Urostigma and *Ficus elastica*. Each possibility represents a separate embodiment of the present invention.

In some embodiments, the basic dye may be New Fuchsin and the acidic dye may be Light Green or Fast green.

In some embodiments, the step of staining the urine sample with New Fuchsin may be followed by staining the urine sample with Light Green or Fast green.

In some embodiments, the method further comprises the step of fixing the urine sample comprising urinary system cells with TCA, prior to the contacting step.

In some embodiments, the one or more components of the *Ficus* extract includes one or more flavonoids.

In some embodiments, the one or more flavonoids include proanthocyanidins.

In some embodiments, the urinary system cells are urothelium cells.

In some embodiments, the urinary system cells are bladder cells.

In some embodiments, the step of identifying urinary system cells having a cytoplasm stained with a predominantly pink to red color is indicative of cellular abnormalities in the bladder pathology.

In some embodiments, the method further comprises the step of analyzing a morphology of the cells having a cytoplasm stained with a predominantly pink to red color.

In some embodiments, the method further comprises the step of contacting the urine sample with an immunostain. In some embodiments, the immunostain may be an anti-Ki67 immunostain.

In some embodiments, the bladder pathology is bladder cancer. In some embodiments, the bladder cancer may be transitional cell carcinoma.

In some embodiments, the method further comprises the step of staining the urine sample with hematoxilin.

In some embodiments, the method further comprises the step of fixing the urine sample comprising urinary system cells with TCA, prior to said contacting and analyzing a morphology of the cells having a cytoplasm stained with a predominantly pink to red color.

In some embodiments, the urine sample is derived from a subject, and wherein identifying urinary system cells having a cytoplasm stained with a predominantly pink to red color indicates that said subject may be afflicted with bladder cancer.

In some embodiments, the bladder cancer may be transitional cell carcinoma.

The present invention successfully addresses the shortcomings of the presently known configurations by providing an accurate and simple approach for detecting abnormal cells in a urinary system of a subject.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DETAILED DESCRIPTION OF THE INVENTION

The present invention relates to methods and kits for detecting abnormal urinary system cells and use thereof in diagnosing a pathology such as bladder cancer.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Bladder cancer (e.g. TCC, squamous cell carcinoma, and adenocarcinoma) is the fifth most common cancer in U.S. TCC is by far the most common form of bladder cancer accounting for more than 90% of bladder cancer cases in the U.S. Bladder cancer is currently diagnosed using cystoscopy and cytology in patients with suspicious symptoms.

A number of urine based tumor markers for identifying malignant cells in the urine are known. However, diagnosis of bladder cancer using such markers requires additional visualization of a tumor via cystoscopy and confirmation by transurethral resection or biopsy. In addition, such markers are highly insensitive to low-grade bladder neoplasms.

PCT Publication No. WO2007/102146 to the present inventors discloses a method of staining or pre-staining cells using an extract of a *Ficus elastica* plant, or active ingredients thereof, for detection of cell abnormalities resulting from cancer or metabolic diseases.

While reducing the present invention to practice, it has been found that the staining approach described in WO2007/102146 was not effective in producing the desired differential staining of urothelial cells. Without wishing to be bound by any theory or mechanism, it is assumed that the known staining was not sufficient for staining cells that are derived from, or suspended in, the hostile environment of the urine. It is also known that harvesting, handling and fixation of cells in a urine sample, or cells derived therefrom, are fundamentally different from the common methods other cells. Accordingly, staining using an extract of *Ficus* plant for identifying abnormal cells was modified and adapted for use in distinguishing between normal and abnormal urothelial cells, such as TCC cells. Calibration and adjustments, including application of basic and acidic dyes, post conditioning, resulted in surprisingly distinct staining which enabled detection of abnormal urothelial cells and low grade TCC. Thus, the current staining method provides an advantageous platform for early detection of urinary system pathologies such as bladder cancer.

Another benefit of the claimed methods and kits is that identification may be carried out in a urine sample despite the relatively low amounts of cells contained therein. This approach further addresses the need for a non-invasive diagnosis of bladder abnormalities.

Thus, there is provided a method of conditioning urinary system cells for identification of abnormal cells.

In some embodiments, there is provided a method of identifying abnormal urinary system cells in a urine sample, the method comprising the steps of:

a. contacting the urine sample with a *Ficus* plant extract or one or more components;

b. staining the urine sample with a basic dye and acidic dye, and     c. identifying urinary system cells having a cytoplasm stained with a predominantly pink to red color as abnormal urinary system cells.

As used herein the phrase "urinary system cells" refers to cells (e.g. epithelial cells) of a kidney, ureter, urethra or bladder.

The cells can may be obtained from, or may be a part of, excised tissue, a smear/scrape (e.g. from a urethra) or a biological sample (e.g. a urine sample, a semen sample).

In some embodiments, the urinary system cells are cells in a urine sample.

The term "cells in a urine sample" refers to cells within a urine sample, a urine sample as is, namely, a urine sample containing cells, cells isolated from a urine sample, or cells derived from a urine sample. This term may also refer to a urine sample enriched for cells.

In some embodiments, the cells may be provided for analysis as a tissue section, a cell suspension, including cells within a urine sample, or a smear.

The thickness of a tissue section can be about 2-50 microns, about 2-20 microns, about 2-10 microns or about 4-5 microns. A smear can be a crude sample of urinary system cells smeared on a microscopic slide without any purification. Other methods for preparation of urine cells for cytology, include, but are not limited to, cytospin or liquid based cytology methods such as ThinPrep™ (Hologic, USA).

In some embodiments, urinary system cells may be also cultured prior to conditioning and staining. In some embodiments, the conditioning and staining are applied on a cells culture of, or derived from, urinary system cells.

In order to increase detection accuracy, the cell sample may be pretreated to remove non-urinary system cells, such as circulatory system cells (e.g. leukocytes and erythrocytes) and the like, using method well known in the art of cell separation (e.g. size exclusion, selective cell lysis etc.).

The method disclosed herein may be effected by contacting the urinary system cells, or a biological sample comprising same, such as, a urine sample, with a *Ficus* plant extract or one or more components thereof thereby conditioning the abnormal cells for identification.

As used herein, the term "conditioning" when used in reference to cells or tissues may be interchangeable with the term pre-staining. Conditioning typically refers to the step of rendering cells (and in particular abnormal cells) more amenable to subsequent detection via histological staining or via biochemical or molecular approaches. The conditioning step of the method disclosed herein may be carried out using an ethanol extract of *Ficus Elastica* leaf tissue.

Contacting the urinary system cell sample with the *Ficus* plant extract or components thereof may be performed by applying it on the urinary system cell sample, or by dipping, soaking and/or incubating the urinary system cell sample in a vessel containing same.

Contacting may be effected for a time period which enables conditioning of abnormal cells, thereby enabling the detection and identification of the abnormal cells upon further staining the conditioned cells with basic and an acidic dye.

In some embodiments, contacting the urinary system cell sample with the *Ficus* plant extract may be performed under ambient conditions. In some embodiments, contacting may be performed for about 1-20 minute or more under ambient conditions or elevated heat and pressure.

The term "ambient conditions" as used herein refers to the common temperature and pressure in a room. These conditions typically include a temperature of about 25° C. (298.15 K, 77° F.) and pressure of about 1 atmosphere.

As used herein, the phrase "*Ficus* plant extract" refers to an ethanol/methanol extract from whole or cut/ground plant tissue (e.g. leaves) of a *Ficus* plant preferably from the subgenus Urostigma, more preferably of the *Ficus elastica* species. The ethanol extract of the plant tissue can include about 10% (v/v ethanol in water), about 20%, about 30%, about 40%, about 50% ethanol, about 60% ethanol, about 70% ethanol, about 80% ethanol about 90% ethanol or about 100% ethanol. Measures should be taken however not to over dilute the extract, as this may affect the subsequent staining. Exemplary extraction protocols are described below.

The extract may be produced from dark green leaves, e.g. between 15 and 25 cm in length (as measured from the base of the leaf to the tip) obtained from *Ficus elastica*. For example, 1000 gr sample of leaves may be cut into 1-3 cm$^2$ pieces and washed with deionized water (DIW) and the leaf pieces may be mixed with 70% ethanol (e.g. 3 liters) and maintained for 14 days (room temperature) in a sealed container, in the dark. Thereafter, the liquid may be separated from the solids and maintained for further use at room temperature.

Alternatively, the leaf pieces may be dried, (e.g. in an oven) to a water content of about 4% (65° C. for 24 hours) and the dry leaf material may be blended into a powder (700-1000 micron particle size). The powder may be then used in extraction in a reflux system: 1 hour per extraction, solvent: 70% ethanol, 40° C. About three sequential extractions may be performed, each time the powder may be re-extracted. Exemplary quantities of 70% ethanol in each extraction may be as follow: first—1:5; second—1:4; third—1:3. The three resulting extracts may be mixed, filtered (e.g. in vacuum filter (paper filter No. 40)). The mixed, filtered extract may be evaporated (e.g. in a rotor evaporator under vacuum at 60° C.) until a steady weight is obtained. The resulting powder (final water content—3%) may be blended further in a grinder. The powder extract may be reconstituted for use as a conditioning/pre-staining reagent. The powder may be suspended in 70% ethanol with 1.3% TDS w/v and a final pH of 7.4.

Components of the plant extract may be the active ingredients of the plant (e.g., flavonoids in an oligomeric form or a polymeric form, or proanthocyanidins), which provide the characteristic conditioning abilities described herein. Such components may be isolated from the plant extract or artificially synthesized.

As is mentioned hereinabove, the conditioning step may be followed by a detection step which may be effected using biochemical, molecular or cell/tissue staining approaches. Each possibility represents a separate embodiment of the present invention.

For detection, the cell/tissue sample may be prepared on a slide or used in suspension. Methods of attaching cells to microscopic slides are well known in the art, and include, for example, layering cells (using smear or liquid-based cytology. e.g. ThinPrep™) of the microscopic slides, centrifuging the cells on the slide (e.g., using a cytospin), mounting tissue sections on the slides (e.g., using paraffin-embedded sections), or smearing cells over a microscopic slide. Each possibility represents a separate embodiment of the present invention.

The microscopic slides which include the cell sample may be used as is or may be pre-coated with agents which increase the adhesiveness of the cells to the slide (e.g., poly-L-lysine or silane). The slides may be heated, frozen or subjected to energy of a certain wave-length (e.g., U.V.) in order to increase adhesiveness of the cells to the slide.

In some embodiments, the urinary system cell sample may be fixed with a fixative prior to detection. Methods of fixing cells are well known in the an, and include the use of fixatives such as paraformaldehyde, glutaraldehyde, acetic acid, trichloroacetic acid, and the like.

In some embodiments, the sample is fixed in trichloroacetic acid (TCA) prior to contacting the sample with the plant extract.

Cell suspensions may be analyzed in containers such as dishes, flasks, tubes and the like. The cells may be suspended in water or TRIS-buffered saline (TBS).

Analysis of slides or suspensions may be performed using subjective approaches (e.g. pathologist described in the Examples section which follows), or by using objective approaches (e.g. automated screening) using, for example, optical (image) analysis software. Since the staining approach disclosed herein relies upon color differences (between normal and abnormal cells) as well as differences in morphology, automated analysis may employ computer algorithms designed for automatic detection of such color differences as well as color density/texture, size of color region and the like. One example of an algorithm which can detect cells based on differential staining/color is THREE-COND. An optical detection algorithm can be combined with morphometric detection algorithms in order to improve the reliability of the results.

In some embodiments a computer is used to identify and/or detect such color differences as well as color density/texture, size of color region and the like. In some embodiments, a computer includes a processor, memory and storage, so that identifying and diagnosing steps are capable of being performed by a computer, by a processor or by software executing on a processor. In some embodiments the computer includes a display and/or user interface, so that color differences as well as color density/texture, size of color region and the like as shown on the display and/or user interface.

In some embodiments, a computer can be used to identify urinary system cells having a cytoplasm stained with a predominantly pink to red color as abnormal urinary system cells. Preferably, the automated (computer enabled) detection is combined with cell cytology analysis for assessing whether or not the morphology of the stained cells corresponds to the morphology of normal (healthy) cells or to the morphology of cancer cells.

The present approach may also include a step of immunocytological screening. In recent years, several non-invasive tests for tumor markers have been approved by the U.S. Food and Drug Administration (FDA). Commercially available tests for the diagnosis of bladder cancer include ImmunoCyt/uCyt+, BTA TRAK®, BTA Stat®, NMP22®, NMP22 Bladder-Chek®, and UroVysion™. Such tests may be used to further validate the results obtained by the present staining and morphological analyses, if necessary.

In some embodiments, staining of the cell sample following incubation with the plant extract, may be performed using staining agents (e.g., dyes).

In some embodiments, staining of the conditioned cells with dyes is exerted under conditions which enable unique or differential staining of abnormal cells.

In some embodiments, the dyes are basic and acidic dyes and combinations thereof.

As used herein the phrase "differential staining" refers to staining an abnormal cell or a cell compartment thereof (e.g., cytoplasm) with a different color or tone than a normal cell of the same type.

Examples of dyes that may be used to stain the conditioned cell sample include, but are not limited to, the following dyes: acetyl yellow, Nitro Fast yellow, Acid black, AzoAmido black 10B, Acid blue, Triarylmethane, Water blue I, Acid blue, Triarylmethane, Methyl blue, Acid fuchsin, Triarylmethane Acid fuchsin Acid green, Triarylmethane, Light Green SF yellowish, Acid green, NitrosoNaphthol green B, Acid green, Triarylmethane Light Green SF yellowish Acid magenta, Triarylmethane, Acid fuchsin, Acid orange, Azo Orange G, AzoAzo-eosin, AzoXylidineponceau, Acid red, AzoChromotrope, AzoPonceau, FluoroneErythrosin B, AzoBiebrich scarlet, AzoWoodstain scarlet, Fluorone Eosin Y ws, Fluorone Eosin B, FluoronePhloxine B, Fluorone, Rose bengal, Quinone-Imine, Azocarmine G, Quinone-Imine Azocarmine B, Acid roseine, Acid rubin, Acid violet, Triarylmethane Acid fuchsin, Acid yellow, Nitro Naphthol yellow S, Nitro Fast yellow, AzoTartrazine, Nitro Martius yellow, AzoMetanil yellow, Fluorone Fluorescein Acid yellow S, Nitro Naphthol yellow S, AzoTartrazineAcridine orange, AcridineAcridine orange, Acritlavine, AcridineAcriflavine Alcian blue, Phthalocyanine Alcian blue, Alcian yellow, Azo Alcian yellow, Alcohol soluble, Fluorone Ethyl eosin, eosin Alizarin, Anthraquinone Alizarin, Alizarin blue, Anthraquinone Alizarin blue, Anthraquinone, Anthracene blue SWR, Alizarin carmine, Alizarin red S, Alizarin cyanin BBS, Anthraquinone, Alizarin, cyanin BBS, Alizarolcyanin R, TriarylmethaneChromoxanecyanin R, Alizarin red S, Alizarin purpurin, AnthraquinonePurpurinAluminon, Triarylmethane Chrome violet CG Amido black, Amidonaphthol red, AzoAzophloxineAmidoschwarz, AzoAmido black, Aniline blue WS—Triarylmethane Aniline blue WS Aniline purple, Azin-Mauveine Anthracene blue SWR, Anthraquinone Anthracene blue SWR Anthracene blue SWX, Anthraquinone Alizarin cyanin BBS, Auramine O, DiarylmethaneAuramine O Azo-eosin, AzoAzo-eosin, Azocarmine B, Quinone-Imine Azocarmine B, Azocarmine G, Quinone-Imine Azocarmine B Azoeosin G, AzoAzo-eosin Azoic diazo, Diazonium salt Fast red B Azoic diazo, Diazonium salt Fast blue B Azophloxine, AzoAzophloxineAzovan blue, Azo Evans blue Azure A, Thiazin Azure A, Azure B, Thiazin Azure B Azure C, Thiazin Azure C Basic blue, Triarylmethane Victoria blue 4R Basic blue, Thiazin Methylene blue Basic blue, Oxazin Nile blue A Basic blue, Triarylmethane Night blue Basic blue, Thiazin Toluidine blue O Basic blue, Triarylmethane Methyl green Basic blue, Triarylmethane Victoria blue B Basic brown, Azo Bismarck brown Y Basic fuchsin—Triarylmethane Basic fuchsin Basic green, Triarylmethane Malachite green Basic green, Thiazine Methylene green Basic orange, AcridineAcridine orange Basic red, SafraninSafranin O Basic red, Eurhodin Neutral red Basic red, TriarylmethanePararosanilin Basic violet, Triarylmethane New fuchsin Basic violet, Triarylmethane Crystal violet Basic violet, Triarylmethane Ethyl violet Basic violet, RhodamineRhodamine B Basic violet, TriarylmethaneRosanilin Basic yellow, ThiazoleThioflavine T Basic yellow, DiarylmethaneAuramine O Biebrich scarlet, AzoBiebrich scarlet Biebrich scarlet R, Azo Sudan IV Bismarck brown Y, Azo Bismarck brown Y Brazilein, Natural Brazilein Brazilin, Natural Brazilin Brilliant crocein, AzoWoodstain scarlet Brilliant crystal, AzoPonceau scarlet Calcium red, Anthraquinone Nuclear fast red Carmine, Natural Carmine Carminic acid, Natural Carmine Carmoisine, AzoChromotrope Celestine blue B, Oxazin Celestine blue B China blue, Aniline blue Chlorantine fast, Azo Sirius red, red Cochineal, Natural Carmine Coelestine blue, Oxazin Celestine blue B Chicago blue, azoPontamine sky blue Chrome violet CG, Triarylmethane Chrome violet CG Chromotrope AzoChromotrope Chromoxanecyanin R TriarylmethaneChromoxanecyanin R Congo corinth, Azo Congo corinth Congo red, Azo Congo red Cotton blue, Triarylmethane Methyl blue Cotton red, Azo Congo red Croceine scarlet, AzoBiebrich scarlet Crocein scarlet, AzoWoodstain scarlet Crocein scarlet MOO, AzoWoodstain scarlet Crocin, Natural Saffron Crystal ponceau, AzoPonceau Crystal scarlet, AzoPonceau Crystal violet, Triarylmethane Crystal violet Dahlia, Triarylmethane Hoffman's violet Diamond green B, Triarylmethane Malachite green Direct blue, AzoTrypan blue Direct blue, Azo Evans blue Direct red, Azo Congo red Direct red Azo Congo corinth Direct red, Azo Congo red Direct red, Azo Sirius red F3B Direct red, Azo Sirius red Direct yellow, ThiazoleThioflavine S Durazol blue—AzoDurazol blue Durazol blue—PhthalocyanineDurazol blue Eosin B, Fluorone Eosin B Eosin Bluish, Fluorone Eosin B Eosin, Fluorone Eosin Y ws Eosin Y, Fluorone Eosin Y ws Eosin yellowish, Fluorone Eosin Y wsEosinol, FluoroneEosinol Erie garnet B, Azo Congo corinthEriochromecyanin R, TriarylmethaneChromoxanecyanin R Erythrosin B, FluoroneErythrosin B Ethyl eosin, Fluorone Ethyl eosin Ethyl green, Triarylmethane Ethyl green Ethyl violet, Triarylmethane Ethyl violet Evans blue, Azo Evans blue Fast blue B, Diazonium salt Fast blue B Fast green FCF, Triarylmethane Fast green FCF Fast red B, Diazonium salt Fast red B Fast yellow Nitro Fast yellow Fast yellow extra, Nitro Fast yellow Fast yellow G, Nitro Fast yellow Fat black HB, Azo Sudan black B Fluorescein, Fluorone Fluorescein Food green, Triarylmethane Fast green FCF Gallein, FluoroneGalleinGallamine blue, OxazinGallamine blue Gallocyanin, OxazinGallocyanin Gentian violet, Triarylmethane Methyl violet Ilaematein, Natural HemateinHaematine, Natural Hematein Haematoxylin, Natural Hematoxylin Helio fast rubin BBL, Anthraquinone Nuclear fast red Helvetia blue, Triarylmethane Methyl blue Hematein, Natural HemateinHematine, Natural Hematein Hematoxylin, Natural Hematoxylin Hoffman's violet, Triarylmethane Hoffman's violet Hydrazine yellow, AzoTartrazine Imperial red Fluorone Eosin B Ingrain blue, Phthalocyanine Alcian blue 8GX Ingrain yellow 1, Azo Alcian yellow INT—Tetrazoliumlodonitrotetrazolium salt Kermes Natural Kermes Kermesic acid, Natural Kermes Kernechtrot, Anthraquinone Nuclear fast red Lac Natural Laccaic acid Laccaic acid, Natural Laccaic acid Lauth's violet, ThiazinThionin Light Green, Triarylmethane Light Green SF yellowish Lissamine fast, AzoLissamine fast yellow yellowLissamine green SF, Triarylmethane Light Green SF yellowish Luxol fast blue— PhthalocyanineLuxol fast blue MBS Magenta, TriarylmethanePararosanilin Magenta I, Triarylmethane Rosanilin Magenta II—Triarylmethane Magenta II, Magenta III, Triarylmethane New fuchsin, Malachite green, Triarylmethane Malachite green Manchester brown, Azo Bismarck brown Y Martius yellow, Nitro Martius yellow Mauve, AzinMauveineMauveine, uveineMuveine, AinMauveineMerbromin, Fluorone Mercurochrome, Mercurochrome, Metanil yellow, AzoMetanil yellow, Methylene azure A Thiazin Azure A, Methylene azure B, Thiazin Azure B, Methylene azure C, Thiazin Azure C, Methylene blue, Thiazin Methylene blue, Methylene green, Thiazine Methylene green, Methyl blue, Triarylmethane Methyl blue, Methyl green, Triarylmethane Methyl green, Methyl violet Triarylmethane, Methyl violet, Triarylmethane Methyl violet, Triarylmethane Crystal violet Milling yellow, Azo Milling yellow Mordant blue, TriarylmethaneChromoxanecyanin R Mordant blue, OxazinGallocyanin Mordant blue, Oxazin Celestine blue B Mordant blue, AnthraquinoneAlizarin cyanin BBS Mordant blue, Anthraquinone Anthracene blue SWR Mordant blue, OxazinGallamine blue Mordant red Anthraquinone Alizarin red S Mordant red, Anthraquinone Alizarin Mordant violet, FluoroneGallein Mordant violet, Triarylmethane Chrome violet CG Naphthalene blue, AzoNaphalene blue black black-Naphthol blue black AzoAmido black Naphthol green B, NitrosoNaphthol green B, Naphthol yellow S, Nitro Naphthol yellow S Natural black, Natural Hematein Natural red, AnthraquinonePurpurin Natural red, Natural Kermes Natural red, Natural Carmine Natural red, Anthraquinone Purpurin Natural red, AnthraquinonePurpurin Natural red, Natural Brazilin Natural red, Natural Laccaic acid Natural red, Natural Orcein Natural yellow, Natural Saffron NBT— Tetrazolium Nitro blue salt tetrazolium Neutral red, Eurhodin Neutral red New fuchsin, Triarylmethane New fuchsin Niagara blue, AzoTrypan blue Night blue, Triarylmethane Night blue Nile blue, Oxazin Nile blue A Nile blue A, Oxazin Nile blue A Nile blue sulphate, Oxazin Nile blue A Nile red, Oxazone Nile red Nitro BT, Tetrazolium Nitro blue salt tetrazolium Nitro blue, Tetrazolium Nitro blue tetrazolium salt tetrazolium Nuclear fast red, Anthraquinone Nuclear fast red Oil red O, Azo Oil red O Orange G, Azo Orange G Orcein, Natural OrceinPararosanilin TriarylmethanePararosanilin Perkin's violet, AzinMauveinePhloxine B, FluoronePhloxine B Picric acid Nitro Picric acid Ponceau, AzoXylidineponceauPonceau, AzoPonceau Ponceau B, AzoBiebrich scarlet Ponceau de Xylidine, AzoXylidineponceauPonceau S, AzoPonceau S Pontamine sky—azoPontanmine sky blue blue Primula, Triarylmethane Hoffman's violet Primuline, ThiazolePrimulinePurpurin, AnthraquinonePurpurinPyronin B, PyroninPyronin B Pyronin G, PyroninPyronin Y Pyronin Y PyroninPyronin Y Rhodamine B RhodamineRhodamine B Rosanilin, TriarylmethaneRosanilin Rose bengal, Fluorone Rose bengal Saffron, Natural Saffron Safranin O, SafraninSafranin O Scarlet R, Azo Sudan IV Scarlet red, Azo Sudan IV Scharlach R, Azo Sudan IV Shellac, Natural Laccaic acid Sirius red, Azo Sirius red F3B Sirius red, Azo Sirius red Sirius supra—AzoDurazol blue blue F3R SolochromecyaninR, TriarylmethaneChromoxanecyanin R Soluble blue—Aniline blue Solvent black, Azo Sudan black B Solvent blue—PhthalocyanineLuxol fast blue MBS Solvent red, Azo Sudan III Solvent red, Azo Sudan IV Solvent red, Azo Oil red O Solvent red, Fluorone Ethyl eosin Solvent yellow, Fluorone Fluorescein Spirit soluble, Fluorone Ethyl eosin eosin Sudan III, Azo Sudan III Sudan IV, Azo Sudan IV Sudan black B, Azo Sudan black B Sudan red BK Azo Sudan III Sulfur yellow S, Nitro Naphthol yellow S Swiss blue Thiazin Methylene blue Tartrazine, AzoTartrazineThioflavine S, ThiazoleThioflavine S Thioflavine T ThiazoleThioflavine T Thionin, ThiazinThionin Toluidine blue, Thiazin Toluidine blue O Toluyline red, Eurhodin Neutral red Tropaeolin G, AzoMetanil yellow Trypaflavine, AcridineAcriflavineTrypan blue, AzoTrypan blue Uranin, Fluorone Fluorescein Victoria blue, Triarylmethane Victoria blue Victoria blue B, Triarylmethane Victoria blue B Victoria blue R, Triarylmethane Victoria blue R Victoria green B, Triarylmethane Malachite green Water blue I, Triarylmethane Water blue I Water soluble eosin, Fluorone Eosin Y wsWoodstain scarlet, AzoWoodstain scarlet Xylidineponceau, AzoXylidineponceau Yellowish eosin, Fluorone Eosin Y ws.

In some embodiments, the dyes include any one or more of the basic dye New Fuchsin, the cationic dye Alcian Blue, and the acidic dyes Light Green or Fast Green. Each possibility represents a separate embodiment of the present invention.

New Fuchsin stains abnormal urinary system cells—preconditioned as described herein—with an intense red color, while leaving normal cell stained with a lighter less intense tone of red (light red or pink). Such staining concentrates at the nucleus and cytoplasm and is indicative of an abnormal phenotype.

New Fuchsin is available as powder from various manufacturers.

The preferred concentration of New Fuchsin (for fixed and mounted tissue) may be about 0.05-0.5% (w/v) in a solution of 2-20% (v/v) ethanol in water. Each possibility represents a separate embodiment of the present invention.

New Fuchsin may be used at a concentration of about 0.02% (w/v), about 0.1% (w/v), about 0.2% (w/v), about 0.3% (w/v), about 0.4% (w/v), about 0.5% (w/v), about 0.6% (w/v) or about 0.7% (w/v). Each possibility represents a separate embodiment of the present invention.

New Fuchsin solution may be water and/or ethanol-based and may include about 2% ethanol, about 5% ethanol, about 10% ethanol, about 15% ethanol, about 20% ethanol, about 25% ethanol, about 30% ethanol, about 35% ethanol, about 40% ethanol or about 50% ethanol. Each possibility represents a separate embodiment of the present invention.

Staining the urinary system cell sample with New Fuchsin may be performed by applying the New Fuchsin on the urinary system cell sample, adding it thereto, or by dipping, soaking and/or incubating the urinary system cell sample in a vessel containing same. Staining the urinary system cell sample with New Fuchsin may be effected for a time period which enables differential staining of abnormal cells by New Fuchsin, e.g., at least 5 seconds, at least about 10 seconds, at least about 1 minute, about 1-10 minutes.

Alcian Blue may be used by the present invention in order to reduce the level of non-specific background staining of normal urinary cells or to stain mucins in case of Mucinuria. Moreover, Alcian Blue can serve as a mordant of Light Green, known in its rapid fading, enabling delay of decoloration.

Alcian Blue is available as powder from various manufacturers.

The concentration of Alcian Blue (for fixed and mounted tissue) may be about 0.05-0.5% (w/v) in water.

Alcian Blue may be used at a concentration of about 0.05% (weight per volume (w/v)), about 0.1% (w/v), about 0.2% (w/v), about 0.3% (w/v), about 0.4% (w/v), about 0.5% (w/v). Each possibility represents a separate embodiment of the present invention.

Staining the urinary system cell sample with Alcian Blue may be performed by applying the Alcian Blue to the cell sample or by dipping, soaking and/or incubating the cell sample in a vessel containing this dye. Staining the urinary system cell sample with Alcian Blue can be effected for a time period which enables reducing of non-specific background, staining of Mucins and protecting Light Green from fading (e.g., at least 30 seconds).

In some embodiments, staining with Alcian Blue is effected following staining with New Fuchsin.

The urinary system cell sample may be additionally stained with Light Green or Fast green.

Light Green and fast Green are acidic dyes which stain the cytoplasm of normal cells with green (leaving the cytoplasm of abnormal cells red/pink/purple following New Fuchsin staining). Light Green and Fast green are available in a powder from various manufacturers.

Light Green may be used at a concentration of about 0.02% (w/v), about 0.1% (w/v), about 0.2% (w/v), about 0.3% (w/v), about 0.4% (w/v), about 0.5% (w/v), about 0.6% (w/v), about 0.7% (w/v) about 0.8% (w/v), about 1% (w/v), about 2% (w/v), about 3% (w/v), about 4% (w/v), about 5% (w/v), about 6% (w/v), about 7% (w/v), about 8% (w/v), about 9% (w/v) or about 10% (w/v). Each possibility represents a separate embodiment of the present invention.

The Light Green solution may be water and/or ethanol-based, and may include 1% ethanol, about 5% ethanol, about 10% ethanol, about 15% ethanol, about 20% ethanol, about 25% ethanol, about 30% ethanol, about 35% ethanol, about 40% ethanol, about 50% ethanol, about 70% ethanol. Each possibility represents a separate embodiment of the present invention.

The Light Green stain may be in a solution of about 4% (w/v) in 20% ethanol (when used with fixed and mounted tissue samples). The concentration of Light Green may be folds less for cytological samples (i.e. 0.4% in 2% ethanol).

Fast Green may be used at a concentration of about 0.02% (w/v), about 0.1% (w/v), about 0.2% (w/v), about 0.3% (w/v), about 0.4% (w/v), about 0.5% (w/v), about 0.6% (w/v), about 0.7% (w/v) about 0.8% (w/v), about 1% (w/v), about 2% (w/v), about 3% (w/v), about 4% (w/v), about 5% (w/v), about 6% (w/v), about 7% (w/v), about 8% (w/v), about 9% (w/v) or about 10% (w/v).

The Fast Green solution may be water and/or ethanol-based and may include about 0.01% ethanol, about 5% ethanol, about 10% ethanol, about 15% ethanol, about 20% ethanol, about 25% ethanol, about 30% ethanol, about 35% ethanol, about 40% ethanol, about 50% ethanol, or about 70% ethanol.

In some embodiments, the Fast Green stain utilized by the present method is about 1% in 20% ethanol.

Staining the urinary system cell sample with Light/Fast Green may be performed by applying the Light/Fast Green on the urinary system cell sample, adding it thereto, or by dipping, soaking and/or incubating the urinary system cell sample in a vessel containing same.

Staining the urinary system cell sample with Light/Fast Green may be effected for a time period which enables differential staining of normal cells in green, e.g. for at least seconds, at least about 30 seconds, at least about 1 minute or about 30 seconds to 10 minutes. Each possibility represents a separate embodiment of the present invention.

In some embodiments, staining with Light/Fast Green is effected following staining with New Fuchsin and optionally Alcian Blue.

Staining with New Fuchsin and optionally Alcian Blue and with Light/Fast Green may be effected as follows. Cells may be first stained with New Fuchsin and then washed (e.g. with ethanol) to remove excess stain. The cells may be then stained with Alcian Blue and washed. Finally, cells may be stained with Light/Fast Green and washed. Use of New Fuchsin together with Light/Fast Green provides color contrast (red vs. green) due to the different affinity of the stains to cell components. New Fuchsin has more affinity for cancer and precancerous cells (conditioned as described herein), while Light/Fast Green has more affinity for normal cell (conditioned as described herein). The use of Alcian Blue reduces non-specific background, stains mucins and prevents rapid fading of the stain.

Thus, the present approach enables identification of abnormal cells as well as differentiation between abnormal and normal cells based on color staining differences.

In some embodiments, contacting the urine sample with a plant extract and basic and acidic dyes stains the cytoplasm of abnormal cells with a predominantly pink to red color.

The term "predominantly pink to red color" refers to a stain that is mostly red or pink with very little (about less than 25%) presence of other colors, especially of green, blue and their combinations. This term may be also defined by a subjective cutoff value, or a threshold, wherein above or below that value the color is predominantly pink to red color. Use of a threshold may enable performing the analysis by automated systems.

A cell stained predominantly dark or intense red upon contact with a single stain such as New Fuchsin is identified herein as an abnormal cell, i.e. a positive result (for a pathology) whereas a cell stained predominantly light red to pink is identified herein as a normal cell, i.e. a negative result.

When using the double staining approach, a cell stained predominantly red (any shade/tone of red, e.g. pink/light red to violet or dark red is identified herein as an abnormal cell, i.e. a positive result (for a pathology) whereas a cell stained predominantly green/blue (any shade of green or blue or combinations thereof) is identified herein as a normal cell, i.e. a negative result.

Tissue samples from bladders subjected to the conditioning and double staining steps described herein were analyzed and the results are presented in Example 1 of the Examples section which follows.

The present conditioning and staining approach results in an almost uniform pink/red cytoplasmic color of TCC cells in histological and cytological samples both low and high grade. Normal urothelium uniformly stain green. A relatively small number of areas of TCC stained green or mix (red/green) shows low Ki67 index in contrast with red areas of TCC shows high Ki67 index.

The urinary system cells stained with New Fuchsin and/or Light/Fast Green may be further stained with Hematoxylin (e.g., Hematoxylin Gill solution). Staining with Hematoxylin may be performed for a staining period of about 10 seconds to about 9 minutes in order to counterstain the cell nuclei. This staining time is effected following fixation, prior to application of the *Ficus* extract. This stain highlights additional nuclear ultra structural features.

Additional stains and dyes for identifying biochemical components (e.g. immunostains such as anti-Ki67) or molecular components (e.g. polynucleotide-specific probes) can be used to further establish cell type, cell state and cell origin (especially when obtained from a urine sample). Microscopic analysis can also be used to type the cell origin. Renal tubular epithelial cells are typically larger than granulocytes, contain a large round or oval nucleus and normally slough into the urine in small numbers. Transitional epithelial cells from the renal pelvis, ureter, or bladder have more regular cell borders, larger nuclei, and smaller overall size than squamous epithelium. Renal tubular epithelial cells are smaller and rounder than transitional epithelium, and their nucleus occupies more of the total cell volume.

Thus, some embodiments of the present invention provide a method of conditioning abnormal cells of a urinary system cell sample so as to render such cells more amenable for subsequent detection. Some embodiments of the present invention also provide a unique staining approach which is highly effective in uniquely staining preconditioned abnormal urinary system cells.

The present approach may be utilized for any urinary system pathology associated with the presence of abnormal cells.

One pathology which may be identified using the present approach is bladder cancer. As is described in the Examples section which follows, the present approach proved highly effective in detecting early stage TCC in bladder tissue. Since the chances of surviving bladder cancer dramatically increase with early detection, the present approach provides physicians with an important diagnostic tool in the fight against bladder cancer.

Thus, there is provided a method of identifying in a subject in need thereof a bladder pathology which is characterized by presence of cell abnormalities. In some embodiments, the bladder pathology may be bladder cancer and the subject may be suspected of having, or as being predisposed to, such a pathology.

As used herein, the term "subject in need thereof" may refer to a mammal, an animal or human subject who is at risk of having a bladder pathology, including, but not limited to, a subject genetically predisposed to bladder pathology, a subject with medical and/or family history of bladder pathology, a subject who has been exposed to any one or more of carcinogens, occupational hazard, environmental hazard and/or a subject who exhibits suspicious clinical signs of bladder pathology, including, but not limited to, blood in urine (hematuria)—urine may appear dark yellow, bright red or brown colored, or urine may appear normal, but blood may be detected in a microscopic examination of the urine; frequent urination; painful urination; back pain; pelvic pain, anemia and/or general weakness. Additionally or alternatively, the subject in need thereof may be a healthy human subject undergoing a routine well-being checkup. The subject in need thereof may also be an animal model, such as, an animal model for bladder cancer or for a disease or disorder associated with bladder cancer or predisposition to bladder cancer.

The method may be effected by contacting bladder cells (biopsy or urine cells) with a *Ficus* plant extract thereby conditioning the abnormal cells for identification. Following conditioning the bladder cells may be stained with a basic and/or acidic dye, such as, New Fuchsin and Light/fast Green. Following staining, the cell sample may be subjectively or objectively analyzed as described herein to identify a bladder cell or cells with a cytoplasm which is stained pink to red/violet. Such a cell is considered abnormal and indicative of a bladder pathology, such as, bladder cancer.

The cell sample may then be further analyzed morphologically or tested for the presence of cancer-specific markers.

A tissue biopsy may be effected via cystoscopy. Briefly, the urethra of the subject may be cleansed and numbed. A cystoscope (e.g. standard rigid cystoscope) may be then inserted through the urethra into the bladder and water or saline is administered through the cystoscope and into the bladder. As fluid fills the bladder, it stretches the bladder wall, enabling view of the entire bladder wall and identification of suspicious lesions/growths etc. A sample of suspicious tissue may be then collected and retrieved using the cystoscope.

A urine sample may be obtained from midstream urine or collected during cystoscopy. The sample may be fixed (for example with 50% ethanol) and then processed using cytospin, a membrane collection method, or a liquid based cytology preparation method.

The cell sample may be analyzed for both color and morphology. Color analysis may be performed as described herein, green cytoplasmic color implies negative for malignancy, and pink to red cytoplasmic color implies positive for malignancy.

TCC morphological criteria may be determined as known in the art. Briefly, low-grade papillary urothelial carcinomas may be characterized by an orderly appearance both architecturally and cytologically. The cells may be evenly spaced and cohesive. There is minimal but definite evidence of nuclear atypia consisting of scattered hyperchromatic nuclei, infrequent mitotic figures predominantly toward the base, and mild variation in nuclear size and shape. High-grade papillary urothelial cancers contain cells that may be dyscohesive with large hyperchromatic nuclei. Some of the tumor cells show frank anaplasia. Mitotic features, including atypical ones, are frequent. Dysplasias were identified according following criteria: change of urothelial polarization, variation in nuclear size, nuclear crowding.

The agents of the present invention described herein may be included in a diagnostic kitiarticle of manufacture preferably along with appropriate instructions for use and labels indicating regulatory approval for use in diagnosing and staging bladder cancer, monitoring for disease recurrence, screening of patients at risk.

In some embodiments, there is provided a kit for identifying abnormal urinary system cells in a urine sample, the kit comprising at least one first container containing a composition comprising a plant extract, at least one second container containing a composition comprising a basic dye; and at least one third container containing a composition comprising an acidic dye.

In some embodiments, the kit further comprises instructions for use of each composition in the first, second and third container, for staining cell preparations (slides, suspensions, smears, a urine sample), and instructions for interpreting the results. In some embodiments, the instructions may further recite a web site address providing further information, troubleshooting, image databases and diagnostic services (for uploaded images). In some embodiments, the instructions are on paper form such as a package insert or label.

The terms "comprises". "comprising", "includes", "including", "having" and their conjugates mean "including but not limited to". The terms "comprises" and "comprising" are limited in some embodiments to "consists" and "consisting", respectively. The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure. In the description and claims of the application, each of the words "comprise" "include" and "have", and forms thereof, are not necessarily limited to members in a list with which the words may be associated.

As used herein, the singular form "a", "an" and "the" include plural references unless the context clearly dictates otherwise. For example, the term "a compound" or "at least one compound" may include a plurality of compounds, including mixtures thereof.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein the term "about" refers to ±10%.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Example 1

Detection of Bladder Cancer Using the Present Approach

A study was designed using the present approach to detect abnormal cells in bladder biopsies with a known pathology. The goal of the present study was to calibrate and optimize the cell conditioning step as well as the staining steps of the present staining approach so as to enable accurate detection of abnormal bladder cells, and in particular enable early diagnosis of bladder cancer.

Material and Method

Sample Collection

Bladder biopsies (archived paraffin blocks) from normal bladder, superficial bladder cancer—Ta, T1, Tis (low grade) and muscle invasive cancer (high grade) were collected and processed as described below. A total of 73 samples were received, 15 samples were not included in the study. All samples received were with a known pathology diagnosis performed at Rabin Medical Center.

Each block was processed by a pathological laboratory to prepare slides for staining. Slides from each block were stained as described below and the staining results were compared to the pathology results of the samples. For each case, one slide was stained by the H&E method for comparative purposes.

H&E Staining

Paraffin-embedded tissue samples were sectioned at 4 microns, and mounted on standard microscopic slides. Deparaffinization was accomplished as follows: immersions in xylene 100%, twice (3 minutes each); ethanol 100%, twice (3 minutes each); immersion in ethanol 95%, twice (3 minutes each); DIW (3 minutes). Sections were stained with hematoxylin, Dye-1, (1 minute), washed in running tap water until the water was clear, and then washed for 10 seconds in running DIW. Sections were then stained in eosin, Dye-C, (1-2 minutes) and washed in tap water and DIW, as above. For cover-slipping, the sections were dehydrated in an ascending series of ethanol concentrations (50%, 70%, 80%, 95%, 100% twice), cleared in xylene 100% (3-4 times), and then mounted in Permount, or an equivalent commercial product.

Staining of Bladder Biopsies

Staining procedures were effected in a slide container. The volume of the solutions used was adjusted to the container size. For deparaffinization, slides were heated to 70° C. for minutes and then immersed in xylene 100%, twice (3 minutes each); ethanol 100%, twice (3 minutes each); ethanol 95%, twice (3 minutes each); water (DIW; 3 minutes). Sections were stained with hematoxylin (1 minute), washed in running tap water until the water was clear, and then washed for 10 seconds in running water (DIW). Sections were then incubated in plant extract solution (4 minutes), washed for 10 seconds in running water (DIW), in 0.5% New Fuschin in ethanol 20%, (2 minutes), washed as above, in 4% Light Green in ethanol 20% (4 minutes) and washed again. For cover-slipping, sections were air-dried for 30 minutes, dipped 3 times in xylene 100% and mounted with Entellan.

Sample Analysis

Each stained sample was analyzed as follows:

(i) Cell color—presence of green/blue colored cells (normal cells), red colored cells (potentially cancer cells) or both. A description of the colors was prepared (mostly green, small amount of red cells, etc).

(ii) Morphological analysis of the cells in the sample was also performed. As indicated above, an important advantage of the present staining approach is that it allows morphological analysis.

An alignment of color and cell morphology was performed and recorded to establish the correlation between cell morphology and cell color. Additional measures were recorded, including color intensity, color shading, spread of colored cells, etc. These measures were analyzed against the other study measures (i.e. cell morphology).

Staining Calibration

The staining protocol was calibrated for optimal incubation parameters, using staining solutions of varying concentrations, different staining sequences and different incubation times. After establishing optimal parameters, an optimized staining approach was generated and tested in order to verify reproducibility. Following several rounds of calibration and testing, the staining approach of the present invention provided highly repetitive results. The calibrated staining protocol was then used for staining of additional samples.

Results

A detailed analysis of resultant staining for each case was prepared and compared to both historical diagnosis as well as to the parallel stained H&E slide.

Each case (both "H&E stained slide" and the slide stained using the present approach) was first analyzed by a professional pathologist. Following completion of the analysis, the slides were transferred to an independent review and analysis by an expert pathologist.

The data from the pathology reports were used to compile the results of the present study.

Table 1 categorizes the cases into the disease groups as depicted in the clinical protocol.

TABLE 1 cases categorized according to clinical diagnosis groups

| Historical diagnosis | Number of cases |
|---|---|
| Normal | 22 |
| Low Grade TCC | 17 |
| High Grade TCC | 19 |

Table 2 compiles the data comparing results of the present staining approach to that of H&E stain, according to the original historical diagnosis:

TABLE 2

Diagnostic agreement rates for the present approach and H&E on bladder biopsies

| Pathologist | Normal (22 cases) | | Low Grade TCC (17 cases) | | High Grade TCC (19 cases) | |
|---|---|---|---|---|---|---|
| | the present approach | H&E | the present approach | H&E | the present approach | H&E |
| 1 | 19/22 [a,b] (86.4%) | 19/22 [a,b] (86.4%) | 16/17 [a,d] (94.1%) | 16/17 [a,d] (94.1%) | 18/19 [a,e] (94.7%) | 18/19 [a,e] (94.7%) |
| 2 | 20/22 [a,c] (90.9%) | 20/22 [a,c] (90.9%) | 17/17 (100%) | 17/17 (100%) | 16/20 [a,f] (80%) | 16/20 [a,f] (80%) |

[a] Number of new diagnoses in agreement with original diagnosis per total number examined.
[b] Three cases (historical Normal Urinary Bladder) were diagnosed as dysplasia by a pathologist after examination of both H&E slide and the slide stained using the present approach.
[c] Two cases were diagnosed respectively as Low Grade and dysplasia by a pathologist after examination of both H&E slide and the slide stained using the present approach.
[d] One case (historical Low Grade TCC) was diagsosed as Normal by a pathologist after examination of both H&E slide and the slide stained using the present approach.
[e] Two cases (historical High Grade TCC) were diagnosed respectively as Hyperplasia and Low Grade TCC by a pathologist after examination of both H&E slide and the slide stained using the present approach.
[f] One case and three cases (all historical diagnosis High Grade TCC), were diagnosed respectively as Hyperplasia (suspicions Low Grade TCC) and Low Grade TCC by a pathologist after examination of both H&E slide and the slide stained using the present approach.

Analysis of the results showed that for each pathologist, diagnosis using the slides stained with the present approach matched that of the H&E slides. Clearly, H&E staining is non-specific and primarily highlights cell and tissue morphology. Thus, diagnosis of a specific disease by analysis of H&E staining requires thorough investigation of the morphology and should be performed by an expert specializing in pathology, specifically, the pathology of said disease. Advantageously, diagnosis based on the approach of the present invention is highly specific and does not require unique skills and expertise. Moreover, diagnosis based on the approach of the present invention is straightforward and rapid thereby it is time and cost effective. In addition, the staining approach of the present invention maintains tissue and cell morphology thereby allows comparing the stained slides with adjacent slide analyzed by other histological means.

In addition to the analysis of cases, an analysis of tissue regions was also performed. This is possible since in most cases there is more than one distinct region for analysis. This analysis was performed by a pathologist by carefully marking and analyzing each region and comparing the morphological diagnosis of the region to the color diagnosis.

A total of 250 regions from 58 slides were analyzed. Normal regions (n=70, green cytoplasm=positive correlation) included 78.6% of regions with green cytoplasm, 14.3% of regions with red cytoplasm and 7.1% of regions with mixed color cytoplasm. Neoplastic regions (dysplastic+ Low Grade TCC 4 High Grade TCC) (n=180, red cytoplasm=positive correlation) included 15.6% of regions with green cytoplasm, 78.9% of regions with red cytoplasm and 5.6% of regions with mixed color cytoplasm. The results are presented in FIGS. 1-3, 5 and 6.

The present staining approach enabled identification of clear morphological features, thus enabling correlation between color and morphology. The above described region analysis provided a good match between the morphology of each region, and the color as displayed following the present staining approach. An important observation is that in a significant number of regions, there was a mixed color of red and green cells, or even within the cells cytoplasm. This provides another level of color difference.

Thus, the present study succeeded in calibrating and optimizing a previously described staining approach for detection of abnormal bladder cells. The calibrated staining approach of the present invention maximized the differential staining properties and enabled excellent morphological visualization capabilities. This dual analysis trait was able to confer non-inferiority to existing methods tested in this study. A high correlation between color and morphology was found.

These observations conclusively show that the present staining approach which is facilitated by the cell conditioning approach of the present invention can be used to accurately diagnose bladder cancer even in early stages.

Example 2

Anti-K167 Immunostaining

Anti-Ki67 immunostaining was used in order to better understand color morphology analysis and the appearance of a significant number of a mixed color population.

The expression of the human Ki67 protein is strictly associated with cell proliferation. During interphase, the antigen can be exclusively detected within the nucleus, whereas in mitosis most of the protein is relocated to the surface of the chromosomes. The fact that the Ki67 protein is present during all active phases of the cell cycle (G(1), S, G(2), and mitosis), but is absent from resting cells (G(0)), makes it an excellent marker for determining the so-called growth fraction of a given cell population. The fraction of Ki67-positive tumor cells (the Ki67 labeling index) is often correlated with the clinical course of the disease.

Materials and Methods
Sample Collection and Ki67 Immunostaining

Paraffin sections of the bladder biopsies described in Example 1 were used for Ki67 staining. The stain was effected as known in the art, using an anti-Ki67 Rabbit monoclonal antibody (Thermo Fisher Scientific) with a Ventana machine (benchmark/XT ISH#712482). The resultant stain was compared to a duplicate slide stained using the present approach. In addition, slides were also double stained with Ki67 immunostain and the present approach. Double staining was achieved by initial staining with anti-Ki67, as described above, and then treating the slide as described below. Calibration and optimization of the stain was performed as described in Example 1.

A Double Stain of Ki67 and the Present Approach

Deparaffinized, Ki67-stained slides were incubated in plant extract solution (2 minutes) and washed for 10 seconds in running DIW. Slides were then dipped 5 times in 0.05% New Fuschin in ethanol 2%, washed as above, dipped 5 times in 0.4% Light Green in ethanol 2% and washed again. For cover-slipping, sections were air-dried for 30 minutes, dipped 3 times in xylene 100% and mounted with Entellan.

Results

A total of 7 bladder biopsies with historical diagnosis of low grade TCC were stained for Ki67. The results were compared with those obtained using the present approach. Three parameters were considered: cell morphology, cell color and Ki67 index.

Numerous slides included multiple regions; the total number of analyzed regions was 67. The result of the staining analysis is provided in Table 3 below.

TABLE 3 double staining with the present approach and anti-Ki67

| Region diagnosis | Region color | # of regions | Ki67 index |
|---|---|---|---|
| Low grade | red | 41 | High |
| Low grade | mix | 4 | Low |
| Low grade | green | 2 | Low |
| Dysplasia | red | 4 | High |
| Metaplasia | red | 2 | High |
| Metaplasia | mix | 3 | Low |
| Normal | green | 7 | Low |
| Normal | green | 3 | High |
| Normal | red | 1 | Low |

Analysis revealed a very high correlation between the color of the present staining and the Ki67 index.

A perfect match was observed for low grade regions, all the red stained regions exhibited a high Ki67 index, whereas the green stained regions exhibited a low Ki67 index. The color mixed regions (regardless of phenotype) exhibited a low Ki67 index, while dysplastic regions, which are abnormal, stained red and exhibited a high Ki67 index. The results are presented in FIGS. 5-6.

Figure 1A:
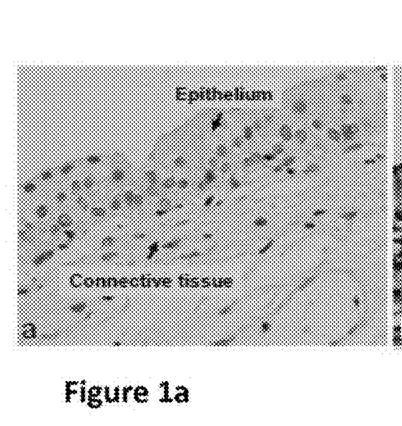
FIGS. 1a-1d illustrate normal bladder epithelium stained with hematoxylin and eosin (H&E), magnified 40× (FIGS. 1a and 1c), or with the present staining approach (FIGS. 1b and 1d). As shown in these figures, normal bladder epithelium stained with the present approach exhibits a uniform green cytoplasmic color.
Figure 1B:
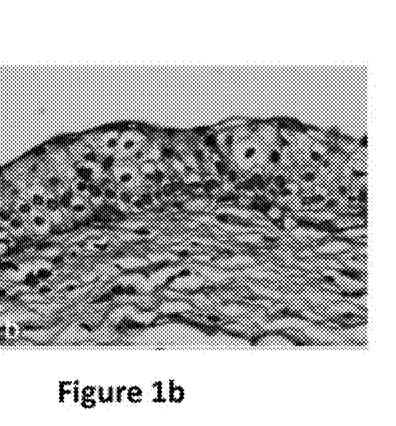
Figure 1C:
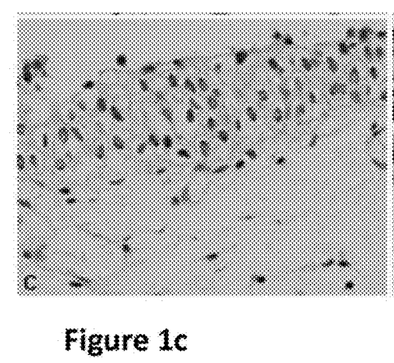
Figure 1D:
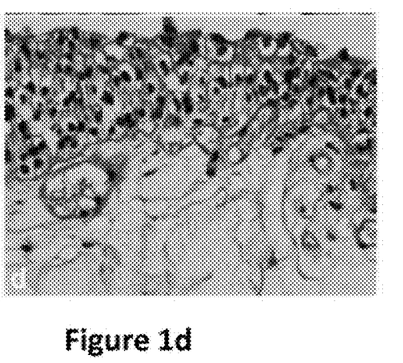
Figure 2A:
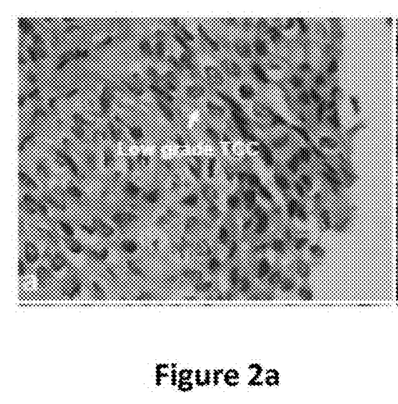
FIGS. 2a-2d illustrate low grade transitional cell carcinoma (TCC) tissue stained with H&E (FIGS. 2a and 2c) or the present approach (FIGS. 2b and 2d); magnified 40×. The cytoplasm of the TCC cells exhibits a unique reddish/violet color when stained with the present approach.
Figure 2B:
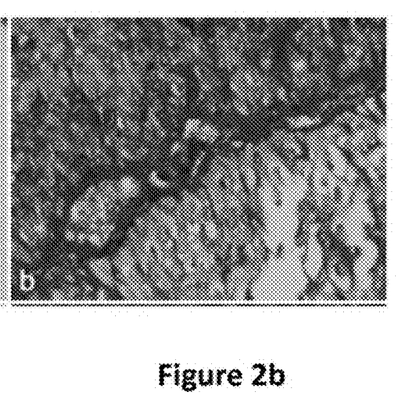
Figure 2C:
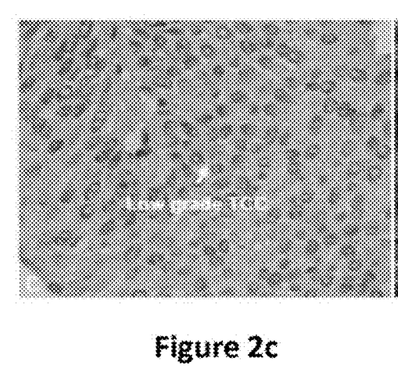
Figure 2D:
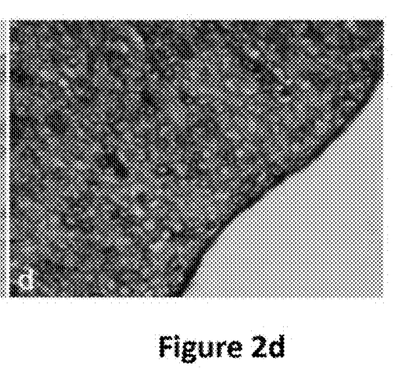
Figure 3A:
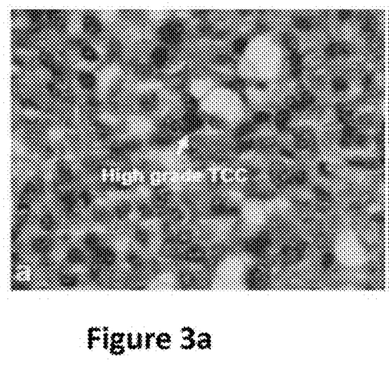
FIGS. 3a-3d illustrate high grade TCC tissue stained with H&E (FIGS. 3a and 3c) or the present approach (FIGS. 3b and 3d); magnified 40×. The cytoplasm of the TCC cells exhibits a unique reddish color when stained with the present approach.
Figure 3B:
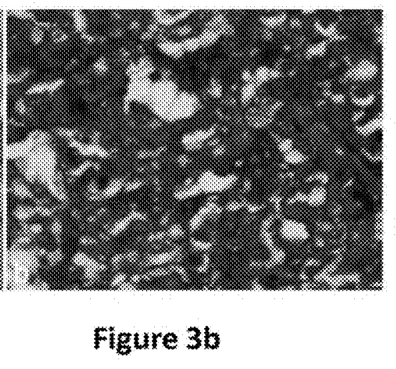
Figure 3C:
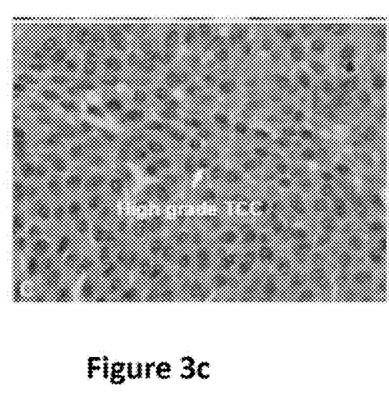
Figure 3D:
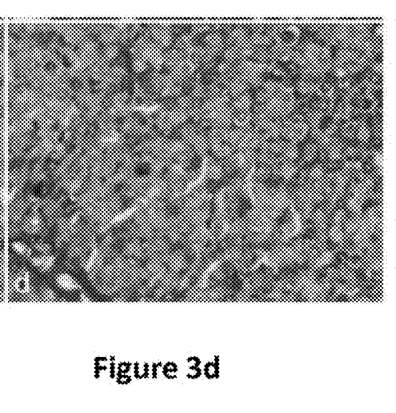
Figure 4A:
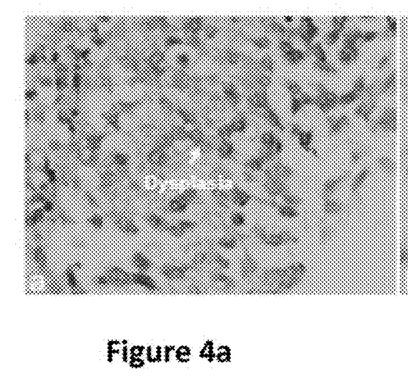
FIGS. 4a-4d illustrate dysplasia of bladder epithelium stained with H&E (FIGS. 4a and 4c) or the present approach (FIGS. 4b and 4d); magnified 40×. The cytoplasm of dysplastic cells exhibits a pink color when stained with the present approach.
Figure 4B:
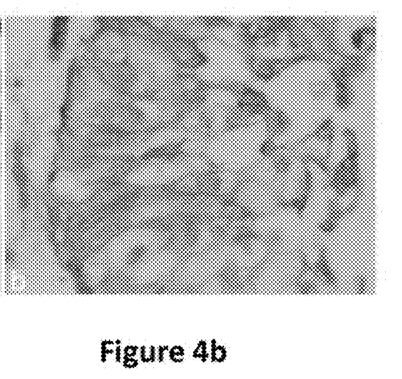
Figure 4C:
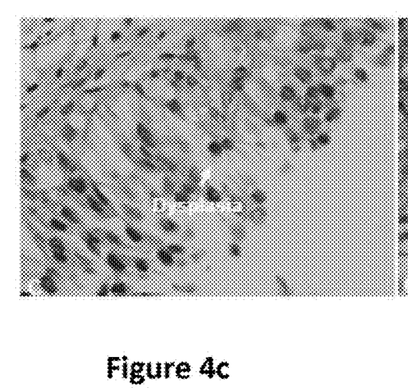
Figure 4D:
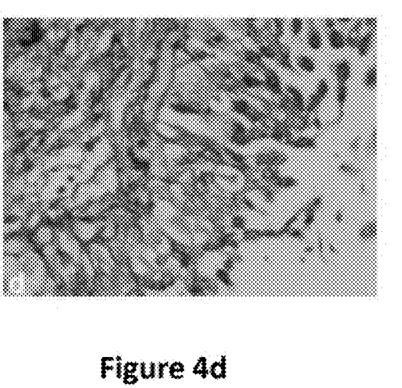
Figure 5A:
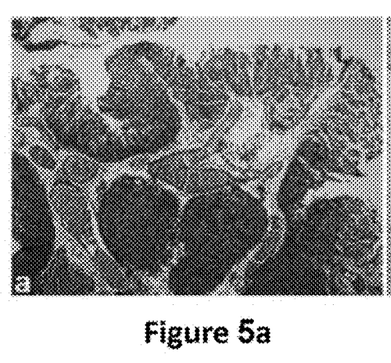
FIGS. 5a-5d illustrate low grade TCC tissue stained with the present approach (FIGS. 5a and 5c) or Ki67 immunostain (FIGS. 5b and 5d), magnified 40×. Cell areas stained in red (FIG. 5a) have a high Ki67 index (FIG. 5b), while cell areas stained in green (FIG. 5c) have relatively low Ki67 index (FIG. 5d).
Figure 5B:
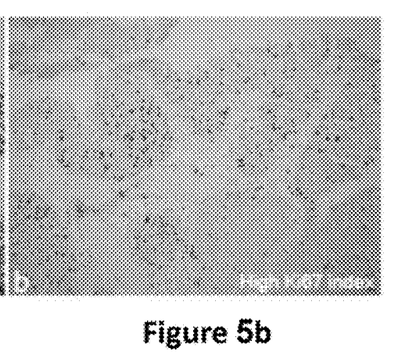
Figure 5C:
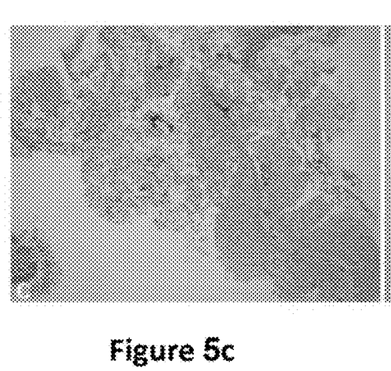
Figure 5D:
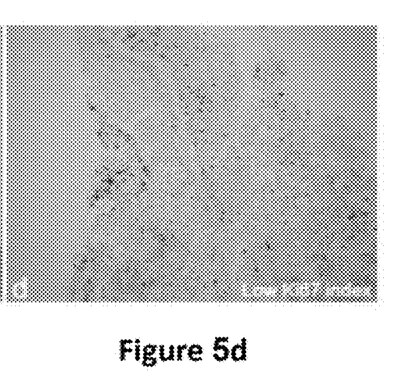
Figure 6A:
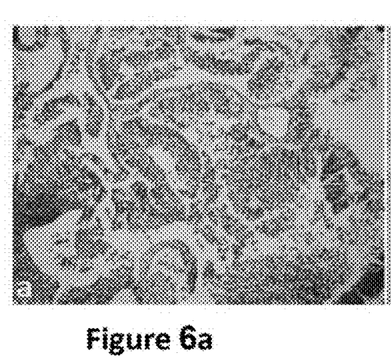
FIGS. 6a-6b illustrate low grade TCC tissue stained with the present approach (FIG. 6a) or Ki67 (FIG. 6b), magnified 10×. The cell cytoplasm is stained with a mix of red and green (FIG. 6a) and shows relatively low Ki67 index (FIG. 6b).
Figure 6B:
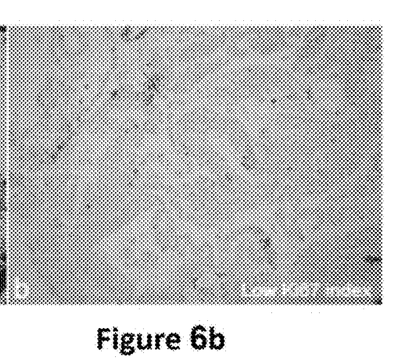
Figure 7A:
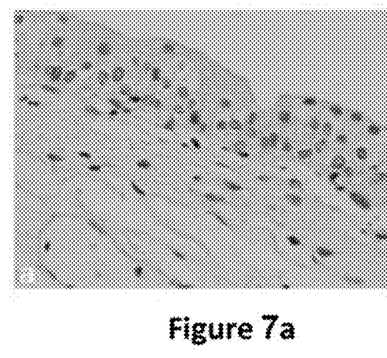
FIGS. 7a-7d illustrate normal bladder epithelium (FIGS. 7a-b) and low grade TCC (FIGS. 7c-d) stained with H&E (FIGS. 7a and 7c) or double stained with Ki67 and the present approach (FIGS. 7b and 7d); magnified 40×. Normal tissue exhibits a blue/green cytoplasmic stain (FIG. 7a) and is devoid of Ki67-positive cells (FIG. 7b). The low grade TCC tissue exhibits a uniform pink cytoplasmic stain (FIG. 7c) and includes numerous Ki67 positive cells (FIG. 7d).
Figure 7B:
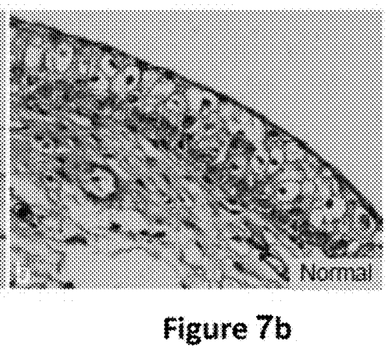
Figure 7C:
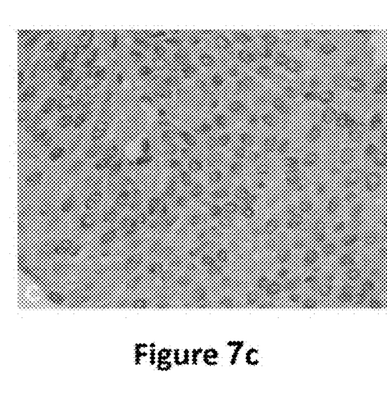
Figure 7D:
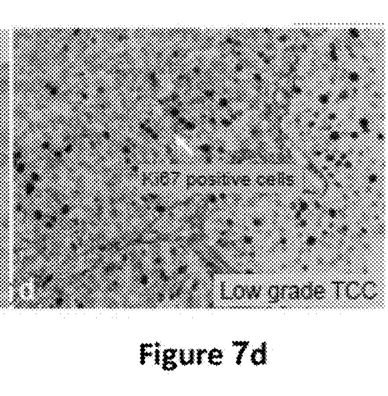

In addition to separately analyzing slides stained with Ki67 or the present approach, slides double stained with anti-Ki67 and the present approach were also analyzed. FIGS. 7b and 7d illustrate the results of such double-stained slides in TCC biopsies. A combination of color staining (as provided by the present approach) and a Ki67 index provides a robust and unique tool which can be especially helpful in cases that are difficult to diagnose, borderline cases. In addition, preservation of morphology, an important feature of the method of the present invention, provides an additional screening tool.

Example 3

Detection of Cancer Cells in Urine Using the Present Approach

Urine contains epithelial cells that are shed from the urinary tract. Urine cytology evaluates the urinary sediment for the presence of cancerous cells from the urinary tract in a convenient, non-invasive manner. The sensitivity of urine cytology is low (reviewed in Mod Pathol. 2009) June; 22 Suppl 2:S53-9), and there is a real need to develop new tests that can be used in bladder cancer screening. The goal of the present study was to calibrate and optimize the cell conditioning step as well as the staining steps of the present staining approach so as to enable accurate detection of abnormal urinary tract cells in a urine sample.

Materials and Methods
Sample Collection

Urine samples from subjects with a known diagnosis were collected and processed by a pathological laboratory to prepare slides for staining using the cytospin method. Slides from each sample were stained as described below. Calibration and optimization of the stain was performed as described in Example 1.

Staining of Urine Cells

Cytospin slides were fixed in TCA 10% (1 hour) and washed for 10 seconds in running DIW. Cells were stained with hematoxylin (1 minute), washed in running tap water until the water was clear, and then washed for 10 seconds in running DIW. Cells were then incubated in plant extract solution (4 minutes), washed for 10 seconds in running DIW, in 0.5% New Fuschin in ethanol 20% (30 seconds), washed as above, in 0.4% Light Green in ethanol 2% (1 minute and 40 seconds) and washed again. For cover-slipping, sections were air-dried for minutes, dipped 3 times in xylene 100% and mounted with Entellan.

Sample Analysis

Stained slides were viewed under the microscope and analyzed as described in Example 1. Briefly, normal and malignant cells were classified according to morphological features and their color was documented. An alignment of color and cell morphology was performed and recorded to establish the correlation between cell morphology and cell color.

Results

Figure 8A:
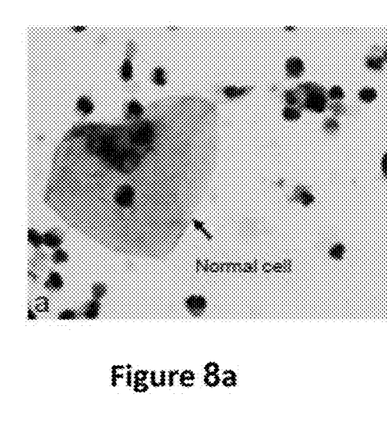
FIGS. 8a-8b illustrate urinary cytology of normal and high grade TCC cells isolated from urine samples, and stained with the present approach; magnified 40×. Cytoplasms of normal epithelial cells (and inflammatory cells) are stained blue/green (FIG. 8a), while cytoplasms of high grade TCC cells are stained red/pink (FIG. 8b).
Figure 8B:
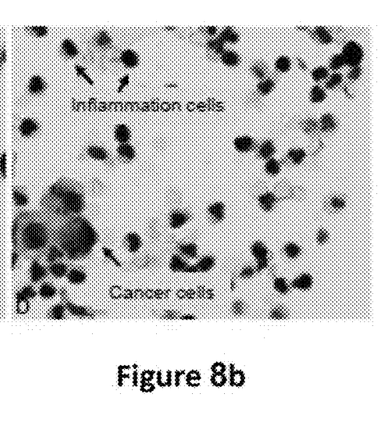

Cytospin slides containing urinary cells were stained with the present approach and carefully examined under the microscope. Cells comprising normal urinary bladder transitional cell epithelium had greenish blue cytoplasm (FIG. 8a). In contrast, morphologically recognizable neoplastic cells exhibited red/magenta tinged cytoplasm (FIG. 8b). Thus, it is possible to recognize neoplasia, even at low magnification, based exclusively on tinctorial status of the epithelium.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A method of identifying cancerous or precancerous cells in a urine sample, the method comprising the steps of:
    (a) fixing a urine sample in tricholoroacetic acid (TCA);
    (b) contacting the urine sample with a *Ficus* plant extract or one or more components thereof after the step of fixing the urine sample in TCA;
    (c) staining the urine sample with a basic dye and acidic dye; and
    (d) detecting whether cells in the urine sample have a cytoplasm stained with a predominantly pink to red color,
    wherein cells having a cytoplasm stained with a predominantly pink to red color is indicative that said cells are cancerous or precancerous cells.

2. The method of claim 1, wherein the *Ficus* plant extract is an ethanol extract of leaf tissue.

3. The method of claim 1, wherein the *Ficus* plant is of a subgenus selected from Urostigma and *Ficus elastica*.

4. The method of claim 1, wherein the basic dye is New Fuchsin and the acidic dye is Light Green or Fast green.

5. The method of claim 4, wherein said staining the urine sample with New Fuchsin is followed by staining the urine sample with Light Green or Fast green.

6. The method of claim 1, wherein the one or more components of the *Ficus* extract includes one or more flavonoids.

7. The method of claim 6, wherein the one or more flavonoids include proanthocyanidins.

8. The method of claim 1, further comprising the step of analyzing a morphology of the cells having a cytoplasm stained with a predominantly pink to red color.

9. The method of claim 1, further comprising contacting the urine sample with an immunostain.

10. The method of claim 9, wherein the immunostain is an anti-Ki67 immunostain.

11. The method of claim 1, further comprising the step of staining the urine sample with hematoxilin.

12. The method of claim 11, wherein the step of fixing the urine sample with TCA is carried out prior to said steps of contacting and analyzing a morphology of the cells having a cytoplasm stained with a predominantly pink to red color.

13. The method of claim 1, wherein the step of contacting the cells in the urine sample with a *Ficus* plant extract or one or more components thereof comprises applying the *Ficus* plant extract on the cells in the urine sample, or by dipping, soaking and/or incubating the cells in the urine sample in a vessel containing same.

14. The method of claim 1, wherein the step of contacting the urine sample is performed for about 1-20 minutes at ambient conditions.

\* \* \* \* \*